(12) United States Patent
Roth et al.

(10) Patent No.: US 9,993,625 B2
(45) Date of Patent: Jun. 12, 2018

(54) BIODEGRADABLE PROTRUSIONS ON INFLATABLE DEVICE

(75) Inventors: Noah Roth, Atlanta, GA (US); Udayan Patel, San Jose, CA (US)

(73) Assignee: MIRUS LLC, Atlanta, GA (US)

( * ) Notice: Subject to any disclaimer, the term of this patent is extended or adjusted under 35 U.S.C. 154(b) by 1422 days.

(21) Appl. No.: 13/203,765

(22) PCT Filed: Jan. 28, 2011

(86) PCT No.: PCT/US2011/022835
§ 371 (c)(1),
(2), (4) Date: Oct. 19, 2011

(87) PCT Pub. No.: WO2011/094476
PCT Pub. Date: Aug. 4, 2011

(65) Prior Publication Data
US 2012/0041412 A1 Feb. 16, 2012

(51) Int. Cl.
*A61M 25/10* (2013.01)
*A61M 37/00* (2006.01)
*A61F 2/958* (2013.01)

(52) U.S. Cl.
CPC ........ *A61M 25/10* (2013.01); *A61M 37/0015* (2013.01); *A61F 2/958* (2013.01); *A61F 2220/0016* (2013.01); *A61F 2250/0031* (2013.01); *A61F 2250/0067* (2013.01); *A61M 2025/1004* (2013.01); *A61M 2025/105* (2013.01); *A61M 2025/1086* (2013.01); *A61M 2037/003* (2013.01); *A61M 2037/0023* (2013.01); *A61M 2037/0046* (2013.01)

(58) Field of Classification Search
CPC .... A61M 2025/105; A61M 2025/1086; A61M 37/0015
USPC ................ 604/103.01, 103.02, 509
See application file for complete search history.

(56) References Cited

U.S. PATENT DOCUMENTS

| | | | |
|---|---|---|---|
| 6,398,804 B1 | 6/2002 | Spielberg | |
| 7,837,670 B2 * | 11/2010 | Barath | ................ 604/517 |
| 8,162,901 B2 * | 4/2012 | Gonnelli | ............. A61B 17/205 |
| | | | 604/151 |
| 2004/0236406 A1 * | 11/2004 | Gregorich | ................ 623/1.16 |
| 2005/0125051 A1 | 6/2005 | Eidenschink et al. | |
| 2006/0198869 A1 | 9/2006 | Furst et al. | |

(Continued)

FOREIGN PATENT DOCUMENTS

| | | |
|---|---|---|
| JP | 2008-104288 | 8/2008 |
| JP | 2010-017214 | 1/2010 |
| WO | 2002043796 | 6/2002 |

OTHER PUBLICATIONS

Intl. Search Report dated Mar. 25, 2011.

*Primary Examiner* — Nathan R Price
*Assistant Examiner* — Anh Bui
(74) *Attorney, Agent, or Firm* — Fay Sharpe LLP

(57) ABSTRACT

A medical device for insertion and expansion in a body passageway. The medical device includes an inflatable device such as a balloon that is designed to be inflated and deflated while positioned in the body passageway. The inflatable device is inflatable by inserting a fluid in an internal cavity of the inflatable device. The inflatable device includes an outer surface that has a surface structure or micro-surface structure which is designed to at least partially penetrate into an inner wall of the body passageway when the inflatable device is inflated.

7 Claims, 4 Drawing Sheets

(56) References Cited

U.S. PATENT DOCUMENTS

| | | |
|---|---|---|
| 2006/0200226 A1 | 9/2006 | Furst et al. |
| 2006/0224237 A1 | 10/2006 | Furst et al. |
| 2007/0123973 A1* | 5/2007 | Roth ........................ A61F 2/91 623/1.15 |
| 2007/0191811 A1* | 8/2007 | Berglund ............ A61M 25/104 604/509 |
| 2009/0048665 A1 | 2/2009 | Miron et al. |
| 2009/0125096 A1 | 5/2009 | Chu et al. |
| 2010/0096778 A1 | 4/2010 | Appleby et al. |
| 2010/0125239 A1* | 5/2010 | Perry et al. ..................... 604/21 |

\* cited by examiner

BIODEGRADABLE PROTRUSIONS ON INFLATABLE DEVICE

The present invention claims priority on U.S. Provisional Patent Application Ser. No. 61/299,584 filed Jan. 29, 2010, which is fully incorporated herein by reference.

BACKGROUND OF THE INVENTION

The invention relates generally to medical devices, and more particularly to an implant for use within a body and, even more particularly to an expandable graft which is particularly useful for repairing various types of body passageways, and still even more particularly to an expandable graft that is at least partially included on one or more surface structures and/or micro-surface structures.

BACKGROUND OF THE INVENTION

Medical treatment of various illnesses or diseases commonly includes the use of one or more medical devices. Two types of medical devices that are commonly used to repair various types of body passageways are an expandable balloon and a stent. These devices are commonly used to reopen or increase the size of an opening in a body passageway such as a blood vessel.

Old age, dietary habits and primary genetics can also lead to a common disease, atherosclerosis. Atherosclerotic plaques and blockages consist of lipids, fibroblasts and fibrin that proliferate and cause obstruction of a vessel. As the obstruction grows, the blood flow diminishes and reaches a level that is insufficient to meet the biological needs of one or more organs. The end result is defined as ischemia.

One purpose of an expandable balloon and a stent is to open a blocked or partially blocked body passageway. When a balloon or stent is used in a blood vessel, the balloon and/or stent is used to open the occluded vessel to achieve improved blood flow which is necessary to provide for the anatomical function of an organ. The procedure of opening a blocked or partially blocked body passageway commonly includes the use of a balloon or stents in combination with other medical devices such as, but not limited to, an introducer sheath, a guiding catheter, a guide wire, etc.

When an expandable balloon is only used to open or increase the opening in a passageway, the expandable balloon generally just compresses the plaque and/or other types of deposits against the sides of the passageway when the balloon is expanded. Although this expansion of the balloon is effective in opening or increasing the opening in the passageway, there is no convenient arrangement to directly treat the diseased region of the passageway with biological agent when only using an expandable balloon.

In view of the existing state of the prior art, there is a need for an inflatable device designed to be expanded in a body passageway which can be used to open or increase the opening in a passageway and to directly treat a diseased region in the passageway with biological agent.

SUMMARY OF THE INVENTION

The present invention is directed to medical devices and more particularly to inflatable devices (e.g., balloons, balloon catheters, etc.) that are insertable into body passageways (e.g., blood vessels, etc.). The medical device is designed to be inflatable when inserted into a treatment area. The inflation of the medical device is designed to increase the size of an opening and/or unblock an opening in the body passageway. The medical device is also designed to locally deliver one or more biological agents at the treatment area when the medical device is inflated to an expanded state.

In one non-limiting aspect of the invention, the medical device includes one or more surface structures or micro-surface structures that are used to facilitate in the operation, function and/or success of the medical device. For example, the one or more surface structures or micro-surface structures can be used to 1) deliver and/or facilitate in the delivery of a biological agent to a treatment area, and/or 2) facilitate in maintaining the medical device in position in a treatment area when the medical device is in an expanded position. The one or more surface structures and/or micro-surface structures can be partially or fully formed of one or more materials that can at least partially dissolve, degrade and/or be absorbed in certain environmental conditions (e.g., exposure to fluids in a body passageway, exposure to enzymes in a body passageway, exposure to air, etc.); however, this is not required. Alternatively, the one or more surface structures and/or micro-surface structures can be partially or fully formed of one or more materials that are biostable and do not dissolve or degrade in a body passageway; however, this is not required.

In another and/or alternative non-limiting aspect of the invention, the one or more surface structures or micro-surface structures on the medical device can be coated with one or more materials; however, this is not required. When the one or more surface structures or micro-surface structures include one or more coatings, such one or more coatings can be used to 1) at least partially control the rate of exposure of the one or more micro-surface structures and/or surface structures to a particular environment (e.g., fluids in a body passageway, gasses in the lungs, bile in a bile duct, in the surrounding atmosphere, etc.), 2) at least partially control the rate at which one or more micro-surface structures and/or surface structures degrades, dissolves and/or is absorbed, 3) at least partially control the rate at which one or more biological agents are released from the one or more micro-surface structures and/or surface structures, 4) form a smooth coating surface on at least a portion of the one or more micro-surface structures and/or surface structures, 5) form a rough coating surface on at least a portion of the one or more micro-surface structures and/or surface structures, 6) facilitate in one or more of the micro-surface structures and/or surface structures to at least partially secure to, engage with and/or penetrate into a body portion, 7) at least partially shield or protect these one or more micro-surface structures and/or surface structures from damage when the medical device is a) packaged and/or stored, b) unpacked, c) inserted into a treatment area, and/or d) handled by a user, 8) increase the bonding and/or adhesion of one or more biological agents, adhesives, marker materials and/or polymers to the one or more micro-surface structures and/or surface structures, 9) change the appearance or surface characteristics of the medical device, and/or 10) increase the ease that the one or more micro-surface structures and/or surface structures penetrates into a body passageway. As can be appreciated, the one or more coatings of material can be designed and/or formulated to have other and/or additional functions.

In still another and/or alternative non-limiting aspect of the invention, the one or more micro-surface structures and/or surface structures and/or one or more coatings on the micro-surface structures and/or surface structures can be formed of a variety of materials (e.g., metals, polymers, biological agents, adhesives, sugars [e.g., glucose, fructose, sucrose, etc.], carbohydrate compounds, paraffins, starches, salts [e.g., NaCl, etc.], etc.). The one or more materials that form the one or more micro-surface structures and/or surface structures and/or one or more coatings of material can be porous, non-porous, biostable, biodegradable (i.e., dissolves, degrades, is absorbed, or any combination thereof in the body), and/or biocompatible. When one or more polymers are used to at least partially or fully make up the one or more micro-surface structures and/or surface structures and/or one or more coatings of material, the one or more polymers can be porous, non-porous, biostable, biodegradable (i.e., dissolves, degrades, is absorbed, or any combination thereof in the body), and/or biocompatible. When one or more layers of polymer are used to at least partially or fully make up the one or more micro-surface structures and/or surface structures and/or one or more coatings of material, the one or more layers of polymer can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers can be polymers that are considered to be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly (glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g., DL-PLA), with and without additives (e.g., calcium phosphate glass), and/or other copolymers (e.g., poly(caprolactone lactide), poly(lactide glycolide), poly(lactic acid ethylene glycol)); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly (iminocarbonate); poly(BPA-iminocarbonate); poly(trimethylene carbonate); poly(iminocarbonate-amide) copolymers and/or other pseudo-poly(amino acids); poly (ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/or copolymers, blends, and/or composites of above. Non-limiting examples of polymers that are considered to be biostable include, but are not limited to, parylene; parylene c; parylene f; parylene n; parylene derivatives; maleic anhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g., polystyrene); poly(vinyl ethers) (e.g., polyvinyl methyl ether); poly(vinyl ketones); poly(vinylidene halides) (e.g., polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronotlex varieties, bionate varieties); vinyl halide polymers and/or copolymers (e.g., polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g., polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyimide; and/or copolymers, blends, and/or composites of above. As can be appreciated, other and/or additional polymers and/or derivatives of one or more of the above listed polymers can be used for the one or more coatings of material.

In yet another and/or alternative non-limiting aspect of the invention, the one or more micro-surface structures and/or surface structures and/or one or more coatings on the micro-surface structures and/or surface structures can be coated with and/or fully be formed of or partially include one or more biological agents. The term "biological agent" includes, but is not limited to, a substance, drug, or otherwise formulated and/or designed to prevent, inhibit and/or treat one or more biological problems, and/or to promote the healing in a treated area. The following categories of biological agents can be used: thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, chemotherapeutic agents, anti-polymerases, anti-viral agents, anti-body targeted therapy agents, hormones, anti-oxidants, radiotherapeutic agents, radiopaque agents and/or radio-labeled agents. As can be appreciated, other or additional types of biological agents can be used. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CS F and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; $T_{H1}$ and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thio-protese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. As can also be appreciated, two or more different biological agents can be used. Typically the amount of biological agent included on, in and/or used in conjunction with the one or more micro-surface structures and/or surface structures and/or one or more coatings on the micro-surface structures and/or surface structures is about 0.01-100 ug per $mm^2$; however, other amounts can be used. The amount of two or more biological agents on, in and/or used in conjunction with the medical device can be the same or different. The one or more biological agents can be coated on and/or impregnated in the one or more micro-surface structures and/or surface structures and/or one or more coatings on the micro-surface structures and/or surface structures by a variety of mechanisms such as, but not limited to, spraying (e.g., atomizing spray techniques, etc.), dip coating, roll coating, sonication, brushing, plasma deposition, depositing by vapor deposition. As can be appreciated, when the one or more micro-surface structures and/or surface structures include one or more biological agents, the one or more micro-surface structures and/or surface structures can be partially or fully grown from the one or more biological agents.

In still yet another and/or alternative non-limiting aspect of the invention, medical device of the present invention can include, but is not limited to, inflatable devices (e.g., balloon, balloon catheter, etc.), stents, grafts, vascular grafts, valves, orthopedic implants, sheaths, guide wires, an orthopedic device, PFO (patent foramen ovale) device, other types of grafts, guide catheter, stent catheters, electrophysiology catheters, other type of implant, a suture, staple, surgical graft, bandage, wrap, balloon catheters, hypotubes, catheters, cutting devices, etc. In one non-limiting embodiment of the invention, the medical device is directed for use in a body passageway. As defined herein, the term "body passageway" is defined herein to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). For vascular applications, the term "body passageway" primarily refers to blood vessels and chambers in the heart. When the medical device is in the form of a stent, the stent can be an expandable stent that is expandable by an inflatable device (e.g., balloon, etc.) and/or other means. The medical device can be at least partially 1) a biodegradable device that at least partially dissolves in the body and/or is absorbed by the body and/or 2) a biostable device that resists or does not dissolve in the body and/or is absorbed by the body. The medical device is typically made of a material that imparts the desirable mechanical properties to the medical device (e.g., strength, durability, expandability, flexibility, hardness, biostability, bendability, coefficient of friction, radial strength, flexibility, tensile strength, tensile elongation, longitudinal lengthening, stress-strain properties, improved recoil properties, radiopacity, heat sensitivity, biocompatibility, etc.). When the medical device is the form of an inflatable device or a stent, the inflatable device or stent can be designed to be insertable to a treatment area in a body passageway and expand in the treatment area.

In a further and/or alternative non-limiting aspect of the present invention, the one or more micro-surface structures and/or surface structures on the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The one or more micro-surface structures can include one or more micro-needles, micro-cylinders, micro-cones, micro-pyramids, microparallelopipes, micro-prisms, micro-hemispheres, etc. on the surface of the medical device. As defined herein, a micro-surface structure is a structure that has at least one dimension (e.g., average width, average diameter, average height, average length, average depth, etc.) that is no more than about 2 mm, and typically no more than about 1 mm. Surface structures are structures that are defined as being larger than micro-surface structures. Typically, the micro-surface structures extend from the outer surface no more than about 400 microns, and more typically less than about 300 microns, and more typically about 15-250 microns; however, other sizes can be used. The micro-surface structures can be clustered together or disbursed throughout the surface of the medical device. Similar shaped and/or sized micro-surface structures can be used, or different shaped and/or sized micro-surface structures can be used. The one or more micro-surface structures can be designed to contain and/or be fluidly connected to a passageway, cavity, etc. in the medical device; however, this is not required. The one or more micro-surface structures can be used to engage and/or penetrate surrounding tissue or organs once the medical device has been positioned on and/or in a patient; however, this is not required. One or more of the micro-surface structures can include one or more internal passageways that can include one or more materials (e.g., biological agent, polymer, etc.); however, this is not required. The one or more micro-surface structures can be formed by a variety of processes (e.g., machining, chemical modifications, chemical reactions, MEMS (e.g., micro-machining, etc.), etching, laser cutting, etc.). The one or more micro-surface structures can be biostable, biodegradable, etc.

In still a further and/or alternative aspect of the present invention, the medical device can be coated with one or more biological agents. A non-limiting list of one or more biological agents that can be coated on the medical device have been previously listed above. The one or more biological agents on the medical device, when used on the medical device, can be released in a controlled manner; however, this is not required. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on the medical device can be controllably released from the medical device and one or more biological agents on the medical device can be uncontrollably released from the medical device. As such, the medical device can be designed such that 1) all the biological agent on the medical device is controllably released, 2) some of the biological agent on the medical device is controllably released and some of the biological agent on the medical device is non-controllably released, or 3) none of the biological agent on the medical device is controllably released. The medical device can also be designed such that the rate of release of the one or more biological agents from the medical device is the same or different. The medical device can also be designed such that the rate of release of the one or more biological agents from the medical device is the same or different. Non-limiting arrangements that can be used to control the release of one or more biological agent from the medical device include a) at least partially coating one or more biological agents with one or more polymers, b) at least partially incorporating and/or at least partially encapsulating one or more biological agents into and/or with one or more polymers, and/or c) inserting one or more biological agents in pores, passageways, cavities, etc. in the medical device and at least partially coat or cover such pores, passageways, cavities, etc. with one or more polymers and/or micro-surface structures. The one or more polymers used to at least partially control the release of one or more biological agent from the medical device can be porous or non-porous. The one or more biological agents can be inserted into and/or applied to one or more micro-surface structures on the medical device, and/or be used to at least partially form one or more micro-surface structures on the medical device. As such, the one or more biological agents on the medical device can be 1) coated on one or more surface regions of the medical device, 2) inserted and/or impregnated in one or more micro-surface structures and/or surface structures, etc. of the medical device, and/or 3) form at least a portion or be included in at least a portion of the one or more micro-surface structures and/or surface structures of the medical device. When the one or more biological agents used on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more micro-surface structures and/or surface structures of the medical device, 1) one or more other coating materials can be applied at least partially over the one or more micro-surface structures and/or surface structures of the medical device, and/or 2) one or more polymers can be combined with one or more biological agents. As such, the one or more biological agents can be 1) embedded in the structure of the medical device; 2) positioned in one or more micro-surface structures and/or surface structures of the medical device; 3) encapsulated between two polymer coatings; 4) encapsulated between the base structure and a polymer coating and/or protective coating; 5) mixed in the base structure of the medical device that includes at least one polymer coating; or 6) one or more combinations of 1, 2, 3, 4 and/or 5. In addition or alternatively, the one or more coatings of the one or more polymers on the medical device can include 1) one or more coatings of non-porous polymers; 2) one or more coatings of a combination of one or more porous polymers and one or more non-porous polymers; 3) one or more coatings of porous polymer, or 4) one or more combinations of options 1, 2, and 3. As can be appreciated different biological agents can be located in and/or between different polymer coating layers and/or on the structure of the medical device. As can also be appreciated, many other and/or additional coating combinations and/or configurations can be used. The concentration of one or more biological agents, the type of polymer, the type of material coating, the type and/or shape of internal structures in the medical device and/or the coating thickness of one or more biological agents can be used to control the release time, the release rate and/or the dosage amount of one or more biological agents; however, other or additional combinations can be used. As such, the biological agent and polymer system combination and location on the medical device can be numerous. As can also be appreciated, one or more biological agents can be deposited on the top surface of the medical device to provide an initial uncontrolled burst effect of the one or more biological agents prior to 1) the controlled release of the one or more biological agents through one or more layers of polymer system and/or 2) the uncontrolled release of the one or more biological agents through one or more layers of polymer system; however, this is not required.

In still another and/or alternative non-limiting aspect of the invention, the medical device can optionally include a protective material that is used to fully or partially cover, embed, and/or coat the one or more of the micro-surface structures and/or surface structures on the medical device. The protective coating generally is coated on both the outer surface of the medical device and the micro-surface structures and/or surface structures on the medical device. The coating thickness of the protective material can be uniform; however, this is not required. For instance, when the protective coating is on both the outer surface of the medical device and the micro-surface structures and/or surface structures, the coating thickness on the outer surface of the medical device may be generally uniform and the coating thickness on the various regions of the micro-surface structures and/or surface structures (e.g., top, top portion, base, bottom portion, middle portion. etc.) can vary. Specifically, when the protective material is applied on the outer surface of the medical device to be generally uniform, since the micro-surface structures extend upwardly from the outer surface, the base of the micro-surface structures will generally have a thicker coating of protective material than the top portion of the micro-surface structures. Generally, the protective material is formed of a different material than the outer surface of the medical device, and/or the micro-surface structures and/or surface structures on the medical device; however, this is not required. Non-limiting examples of materials that can be used to fully or partially form the protective material are polymers, biological agents, adhesives, sugars [e.g., glucose, fructose, sucrose, etc.], carbohydrate compounds, paraffins, starches, salts [e.g., NaCl, etc.], etc. The protective material can optionally include one or more biological agents. The protective material is generally formed of a material that will dissolve and/or degrade faster than the outer surface of the medical device, and/or the micro-surface structures and/or surface structures on the medical device so as to rapidly expose or more fully expose the outer surface of the medical device and the micro-surface structures and/or surface structures on the medical device when the medical device is positioned in the treatment area of the body passageway; however, this is not required. In one non-limiting embodiment of the invention, the one or more coatings of protective material generally follow the profile of the one or more of the micro-surface structures and/or surface structures on the medical device; however, this is not required. In another non-limiting embodiment of the invention, the one or more coatings of protective material have a generally uniform thickness on the outer surface of the medical device, which thickness may be less than equal to or greater than the height of the surface structures and/or micro-surface structures so that such surface structures and/or micro-surface structures are partially or fully embedded under the protective material. In one non-limiting aspect of this embodiment, the coating thickness of the protective material is generally at least about 0.001 µm and typically less than about 500 µm; however, other thickness can be used depending on the size and/or shape of the one or more of the micro-surface structures and/or surface structures on the medical device. In another and/or alternative aspect of this embodiment, the thickness of the one or more coatings of protective material form a coating layer that is about 0.01-150 µm, and typically about 0.1-50 µm; however, it will be appreciated that other thicknesses can be used. In another and/or alternative embodiment of the invention, the one or more coatings of protective material form a coating layer that partially or fully embeds one or more of the micro-surface structures and/or surface structures on the medical device within the one or more coatings of protective material. The coating thickness of such a coating typically depends on the size and/or shape of the one or more of the micro-surface structures, and/or surface structures on the medical device, and/or whether the one or more coatings of protective material are to be partially or fully embedded within the one or more coatings of protective material.

In yet a further and/or alternative non-limiting aspect of the invention, the medical device can include a marker material that facilitates in enabling the medical device to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler like markings on the medical device to facilitate in the positioning of the medical device in a body passageway. The marker material can be a rigid or flexible material. The marker material can be a biostable or biodegradable material.

In another and/or alternative non-limiting aspect of the present invention, the medical device is designed to improve patient procedural outcome. The medical device can be designed to be used as a biological agent delivery mechanism to deliver one or more biological agents to and/or into a wall of a body passageway and/or down stream from the site of implantation of the medical device. In one non-limiting embodiment of the invention, the medical device is designed to deliver one or more biological agents directly into the wall of a body passageway. In another and/or alternative non-limiting embodiment of the invention, the medical device is designed to at least partially utilize molecular diffusion to deliver one or more biological agents to and/or into a wall of a body passageway and/or down stream from the site of implantation of the medical device; however, this is not required. When a molecular diffusion mechanism is used, this mechanism can be used to at least partially control the diffusion of one or more biological agents from the medical device. When a molecular diffusion mechanism is used on the medical device, one or more non-porous polymer layers can be used to facilitate in such molecular diffusion; however, this is not required. In still another and/or alternative non-limiting embodiment of the invention, the medical device is an inflatable device such as a balloon that includes one or more micro-surface structures on the outer surface of the inflatable device. The inflatable device can include at least one layer of biological agent and/or at least one polymer coating on the outer surface of the inflatable device; however, this is not required. The one or more micro-surface structures on the surface of the inflatable device can be partially formed and/or coated with one or more layers of biological agent and/or polymer coating; however, this is not required.

In still another and/or alternative non-limiting aspect of the present invention, the medical device is an inflatable device that includes one or more protrusions (e.g., needles, micro needles, etc.) on the outer surface of the inflatable device. These one or more protrusions are generally biodegradable; however, this is not required. These one or more protrusions generally include or are formed of one or more biological agents. These one or more protrusions are designed to at least partially penetrate into the surface of a body passageway when the inflatable device is expanded in the body passageway. These one or more protrusions can optionally be designed to break-off of the inflatable device after the inflatable device has been expanded in the body passageway and after the one or more protrusions have at least partially penetrated in the body passageway; however, this is not required. These one or more protrusions can optionally be designed to enable fluid (e.g., biological agent, etc.) to flow from the inflatable device, at least partially through the protrusions and into the body passageway after the inflatable device has been expanded in the body passageway and after the one or more protrusions have at least partially penetrated in the body passageway; however, this is not required. Additional non-limiting features of the invention are disclosed in the attached drawings. Additional information regarding the one or more protrusions and formation of the one or more protrusions is disclosed in US Patent Application Nos. 2006/0224237; 2006/0198869; 2007/0123973; 2006/0200226; and US2010/0096778, which are incorporated herein by reference.

In yet another and/or alternative non-limiting aspect of the present invention, the medical device includes an inflatable device that includes one or more protrusions on the outer surface of the inflatable device that are designed to at least partially penetrate into the wall of a body passageway (e.g., blood vessel, etc.) when the inflatable device is expanded in the treatment area of the body passageway. As can be appreciated, none, a portion, or all of the protrusions can be formed of a biodegradable and/or bioabsorbable material. As can also be appreciated, a portion or all of the protrusions on the outer surface of the inflatable device can be designed to at least partially penetrate into the wall of a body passageway. The inflatable device of the present invention can be used as the sole treatment device, or can be used in conjunction with another medical device such as, but not limited to a stent. When the inflatable device is to be used in conjunction with a stent, a first use is that the inflatable device is first positioned and expanded in the treatment area and the stent is subsequently positioned and expanded in the treatment area, and a second use is that the stent is loaded on the inflatable device that the stent and inflatable device are simultaneously positioned in and expanded in the treatment area. In one non-limiting embodiment of the invention, the top portion of the one or more protrusions can include a tapered or sharpened region to facilitate in the penetration of the one or more protrusions into the wall of the body passageway; however, this is not required. The one or more protrusions can be formed in a variety of ways (e.g., molding, etching, growing, laminating, stamping, MEMS processes, lithographic techniques, inkjet technology, etc.). The size and/or shape of the one or more protrusions can be the same or different. The distribution of a plurality of protrusions on the outer surface of the inflatable device can be uniform or non-uniform. As can be appreciated, certain patterns of protrusions can be formed on the outer surface of the inflatable device. As can be appreciated, a portion or all of the protrusions can include a tapered or sharpened region to facilitate in the penetration of the one or more protrusions into the wall of the body passageway. The shape of the tapered or sharpened region on the one or more protrusions, when used, is non-limiting. In one non-limiting configuration, the shape of the tapered or sharpened region on the one or more protrusions is similar to a needle point. In another non-limiting configuration, the shape of the tapered or sharpened top region on the one or more protrusions is similar to an arrow head. In still non-limiting configuration, the shape of the tapered or sharpened top region on the one or more protrusions is designed to penetrate into the wall of a body passageway, but resist being removed from the body passageway once partial or full penetration of the body passageway has occurred. In another and/or alternative non-limiting embodiment of the invention, all or a portion of the one or more protrusions can be designed to break off from the remaining body of the one or more protrusions and/or from the outer surface of the inflatable device. Such a design of the one or more protrusions can result in all or a portion of the one or more protrusions remaining partially or fully embedded in the wall of the body passageway after the inflatable device is deflated and removed from the treatment area of the body passageway. When the one or more protrusions includes and/or is at least partially formed of one or more biological agents, the portion of the one or more protrusions remaining embedded in the body passageway can be used to continue to locally supply biological agent to the treatment area of the body passageway after the inflatable device is removed from the treatment area. As can be appreciated, a portion or all of the protrusions include and/or are partially or fully formed of biological agent. As can also be appreciated, a portion or all of the protrusions may be absent biological agent. In one non-limiting configuration, the shape of the top region on the one or more protrusions can be designed to break off from the remaining body of the one or more protrusions. The one or more protrusions can include one or more notches, narrowed regions, etc. to facilitate in the breaking off of the tapered or sharpened top region from the remaining body of the one or more protrusions. In another and/or alternative non-limiting configuration, the body of the one or more protrusions can be designed to break off from the remaining body of the one or more protrusions, and/or the body of the one or more protrusions can be designed to break off from the outer surface of the inflatable device during or after the one or more protrusions have partially or fully penetrated into the wall of the body passageway. The one or more protrusions can include one or more notches, narrowed regions, etc. to facilitate in the breaking off of the body from another portion of the body and/or the outer surface of the inflatable device; however, this is not required. Also, or alternatively, the one or more protrusions can be formed of different materials in different regions of the protrusions, wherein the type of materials and/or the regions the materials are used in facilitate in the breaking of the protrusion at a certain location or region; however, this is not required. In still another and/or alternative non-limiting embodiment of the invention, the one or more protrusions can include one or more internal fluid passageways that enable fluid from the inflatable device to flow through the one or more internal fluid passageways. Such an arrangement can be used to enable fluid such as, but not limited to, fluid containing biological agent, to be conveyed from the inflatable device through the one or more protrusions and then locally to and/or into a treatment area on the body passageway. As can be appreciated, none, a portion, or all of the protrusion can include one or more internal fluid passageways. In one non-limiting configuration, the body of the inflatable device includes one or more passageways or openings through or on the outer surface of the inflatable device to enable fluid in the interior of the inflatable device to flow through the one or more passageways or openings to the outer surface of the inflatable device. One or more of the protrusions are positioned partially or fully over the one or more passageways or openings in the inflatable device so that fluid flowing though one or more passageways or openings can proceed to at least partially flow though the one or more internal fluid passageways in the one or more of the protrusions. In such an arrangement, the inflatable device can be positioned at a treatment area in the body passageway and then inflated. A fluid can be used to inflate the inflatable device at the treatment area of the body passageway. During and/or after inflation of the inflatable device, one or more biological agents can be conveyed to the inflatable device. The one or more biological agents in the inflatable device can then flow though one or more passageways or openings in the inflatable device and to the outer surface of the inflatable device to provide biological agent locally at the treatment area. When the inflatable device is sufficiently expanded to cause one or more of the protrusions to penetrate into the wall of the body passageway, if the one or more protrusions are designed to include internal fluid passageways that are in fluid communication with some or all of the one or more passageways or openings in the inflatable device, the one or more protrusions can be used to convey all or a portion of the one or more biological agents, that flow through the one or more passageways or openings in the inflatable device and then through the one or more internal fluid passageways in the one or more protrusions, locally into the wall of the body passageway. In another and/or alternative configuration, the one or more protrusions that include the one or more internal fluid passageways can include a removable or breakable portion that enables fluid to flow through the one or more internal fluid passageways once the removable portion separates from the remaining portion of the protrusion or once the protrusion breaks. In this non-limiting configuration, the free flow of fluid though the one or more internal fluid passageways of the one or more protrusions can be inhibited or prevented until the removable portion separates from the remaining portion of the protrusion or once the protrusion breaks. The removable portion of the one or more protrusions, can be designed in may ways. In one non-limiting design, the removable portion separates from the remaining portion of the protrusion once the fluid pressure in the one or more internal fluid passageways is sufficiently great enough to cause the separation from the remaining portion of the protrusion. In another and/or alternative non-limiting design, the removable portion separates from the remaining portion of the protrusion by the removable portion rapidly dissolving or degrading. In still another and/or alternative non-limiting design, the removable portion includes one or more structures and/or adhesives that resist release from the body passageway once the removable portion has contacted the body passageway and/or has partially or fully penetrated into the body passageway; however, this is not required. Such resistance to being released from the body passageway results in the removable portion being dislodged from the remainder of the protrusions during penetration and/or after penetration of the removable portion into the body passageway. Such structures can include barbs, fibers and/or other non-smooth surfaces. In yet another and/or alternative non-limiting design, the removable portion can be designed to be released from the remaining portion of the protrusion by an electrical charge, by electromagnetic radiation, ultrasonic waves, and/or by a chemical reaction; however, this is not required. As can be appreciated, these other release mechanisms can be used in conjunction with fluid pressure; however, this is not required.

In still yet another and/or alternative non-limiting aspect of the present invention, the medical device includes an inflatable device that includes one or more protrusions on the outer surface of the inflatable device and which a plurality of the protrusions are at least partially protected from damage during the insertion of the inflatable device into a body passageway by the folding of the inflation device. A plurality of the protrusions are positioned in the folds of the inflatable device so that when the unexpanded inflatable device is inserted into a body passageway and to the treatment area, the folds of the inflatable device shield and protect one or more protrusions located in the folds from contact with the body passageway, this protects the protrusion from damage until the inflatable device is positioned at the treatment area and the inflatable device is expanded.

In one non-limiting overview of the present invention, there is provided a medical device that is adapted for introduction into a patient. The medical device can be designed to include and/or to release one or more biological agents in a controlled and/or uncontrolled fashion; however, this is not required. For instance, all of the biological agent can be controllably released from the medical device, all of the biological agent can be uncontrollably released from the medical device, or some of the biological agent can be controllably released and some uncontrollably released from the medical device. The controlled release of the one or more biological agents can be by molecular diffusion through one or more polymer layers; however, it will be appreciated that other, or additional mechanisms can be used to control the rate of release. The polymer and/or biological agent that is included on and/or forms at least a portion of the medical device can be hydrophobic or hydrophilic, which can be used to facilitate in the controlled release of the one or more biological agents; however, this is not required. The thickness of the one or more polymer layers can be selected to facilitate in the controlled release of the one or more biological agents; however, this is not required. The molecular weight and/or molecular structure of the one or more biological agents and/or one or more polymers can be selected to facilitate in the release of the one or more biological agents; however, this is not required. The medical device can have a variety of applications such as, but not limited to placement into the vascular system, esophagus, trachea, colon, biliary tract, or urinary tract. As can be appreciated, the medical device can have other or additional uses. The medical device can include one or more layers of polymer and/or biological agent on the surface structure of the medical device; however, this is not required. At least one biological agent can be deposited underneath and/or combined with at least one non-porous polymer layer so as to control the release of the at least one biological agent; however, this is not required. The medical device can also include one or more porous polymers; however, this is not required. One or more polymer layers, when used, can be applied by vapor deposition, plasma deposition, or another or additional coating technique. The medical device can be in the form of an inflatable balloon. The medical device can include one or more surface structures and/or micro-surface structures that can include and/or be at least partially formed by one or more biological agents and/or polymers. These structures can be at least partially formed by MEMS (e.g., micro-machining, etc.) technology, layer growing processes, and/or other types of technology. The structures can be designed to contain and/or be fluidly connected to a passageway in the medical device; however, this is not required. The micro-surface structures can be designed to engage and/or penetrate surrounding tissue or organs once the medical device has been positioned on and/or in a patient and inflated; however, this is not required. One or more polymers and/or biological agents can be inserted in these surface structures and/or at least partially form these surface structures and/or micro-surface structures of the medical device; however, this is not required. Typically, the micro-surface structures, when formed, extend from or into the outer surface no more than about 400 microns, and more typically less than about 300 microns, and more typically about 15-250 microns; however, other sizes can be used. The micro-surface structures can be clustered together or disbursed throughout the surface of the medical device. Similar shaped and/or sized micro-surface structures can be used, or different shaped and/or sized micro-surface structures can be used. The surface topography of the medical device can be uniform or vary to achieve the desired operation and/or biological agent released from the medical device. As can be appreciated, the medical device or one or more regions of the medical device can be constructed by use of one or more microelectromechanical manufacturing techniques (MEMS (e.g., micro-machining, etc.)), layer growing techniques, molding techniques; however, this is not required. As can be appreciated one or more biological agents and/or polymers can be placed on different regions of the medical device to achieve the desired operation and/or biological agent released from the medical device. The medical device can be used in conjunction with other biological agents. For instance, one or more biological agents can be injected into the medical device (e.g., inflatable device, etc.), and such injected biological agents can be released from the medical device (e.g, released through one or more surface and/or micro-surface structures, released form one or more openings in the body of the inflatable device, etc.). The introduction of biological agents from a source other than the medical device can have a synergistic effect which can enhance the success of the medical device. The medical device of the present invention can be used to provide localized delivery of a therapeutic agent in both de-novo lesions and for in-stent restenosis. The medical device can include one or more protrusions (e.g., needles, etc.) that are able to penetrate the vasculature and optionally detach, leaving behind a portion that is made of or includes a polymer/biological agent. A bolus of biological agent can also be provided during such procedure. The biological agent can be formulated to relieve restenosis, thrombus formation, inflammation, etc.; however, this is not required.

One non-limiting object of the present invention is the provision of a medical device that includes an inflatable device that includes one or more surface structures or micro-surface structures.

Another and/or alternative non-limiting object of the present invention is the provision of a medical device that includes an inflatable device that includes one or more surface structures or micro-surface structures, which one or more surface structures or micro-surface structures include and/or are at least partially formed of one or more biological agents and/or one or more polymers.

Still another and/or alternative non-limiting object of the present invention is the provision of a medical device that includes an inflatable device that includes one or more surface structures or micro-surface structures, which one or more surface structures or micro-surface structures are designed to at least partially penetrate into a body passageway.

Yet another and/or alternative non-limiting object of the present invention is the provision of a medical device that includes an inflatable device that includes one or more surface structures or micro-surface structures, which one or more surface structures or micro-surface structures are designed to at least partially penetrate into a body passageway and at least a portion of the surface structures or micro-surface structures is to break-off or detach from another portion of the surface structures or micro-surface structures or detach from the inflatable device and then remain in the penetrated wall of the body passageway.

Still yet another and/or alternative non-limiting object of the present invention is the provision of a medical device that includes an inflatable device that includes one or more surface structures or micro-surface structures, which one or more surface structures or micro-surface structures are designed to at least partially penetrate into a body passageway and locally deliver one or more biological agents in a treatment area.

These and other advantages will become apparent to those skilled in the art upon the reading and following of this description taken together with the accompanying drawings.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
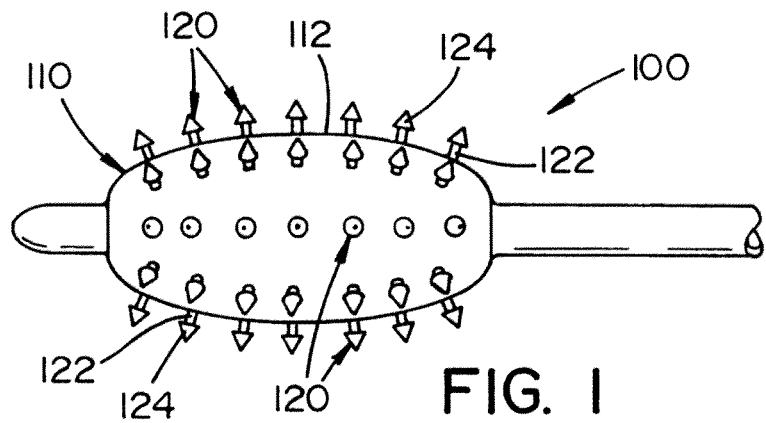
FIG. 1 is a side view of an inflatable device that includes one non-limiting embodiment of a plurality of surface structures or micro-surface structures on the outer surface of the inflatable device in accordance with the present invention.

Referring now to the drawings wherein the showings are for the purpose of illustrating embodiments of the invention only and not for the purpose of limiting the same, FIGS. 1-11 illustrate various non-limiting embodiments of an inflatable medical device that includes one or more surface structures or micro-surface structures in accordance with the present invention. The present invention will be described with particular reference to one or more surface structures or micro-surface structures used in association with an inflatable medical device such as, but not limited to a balloon catheter; however, it will be appreciated that the one or more surface structures or micro-surface structures can be used in association with certain types of expandable medical devices (e.g., stents, etc.).

Figure 10:
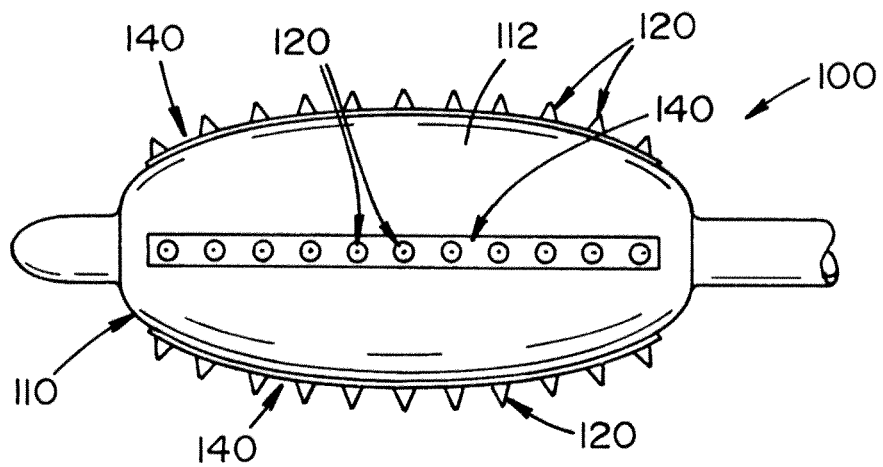
FIG. 10 is a side view of an inflatable device that includes another non-limiting embodiment of a plurality of surface structures or micro-surface structures organized in a certain pattern on the outer surface of the inflatable device in accordance with the present invention; and, FIG. 11 is a side view of an inflatable device that includes another non-limiting embodiment of a plurality of surface structures or micro-surface structures organized in a certain pattern on the outer surface of the inflatable device in accordance with the present invention.
Figure 11:
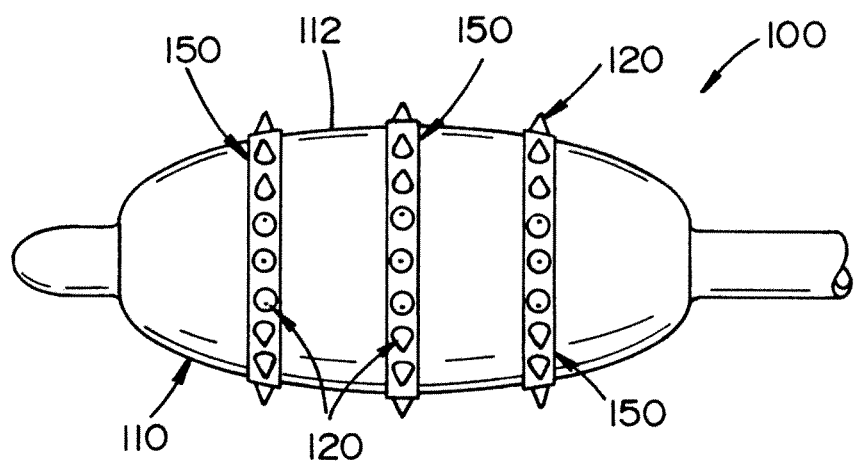

Referring now to FIG. 1, there is illustrated a balloon catheter 100. The balloon catheter includes an inflatable balloon 110 at or near the end of the balloon catheter. The design, size, shape, and materials used for the balloon catheter are non-limiting. The use and construction of balloon catheters are well known in the art, thus will not be described in detail herein. Balloon catheters are generally inserted through a body passageway (e.g., blood vessel, etc.) and to a treatment area (e.g., diseased area, etc.) while the inflatable balloon on the balloon catheter is in a partially for fully deflated state. When the inflatable balloon on the balloon catheter is positioned at the treatment area, the inflatable balloon is partially or fully inflated. After partial or full inflation of the inflatable balloon, the inflatable balloon is partially or fully deflated and then removed from the treatment area. The balloon has an outer surface 112 that includes a plurality of surface structures or micro-surface structures 120. The number of surface structures or micro-surface structures on the outer surface 112 and/or the orientation of the surface structures or micro-surface structures on the outer surface 112 is non-limiting. For example, FIG. 1 illustrates that the plurality of surface structures or micro-surface structures on the outer surface are spaced uniformly over the entire outer surface of the inflatable balloon. FIG. 8 illustrates that the plurality of structures or micro-surface structures are grouped together in discreet segments 130 that are spaced uniformly from one another on the outer surface of the inflatable balloon. The discreet segments can include one or more surface structures or micro-surface structures. FIG. 8 illustrates that each segment includes four (4) surface structures or micro-surface structures; however, this is not required. All of the segments can contain the same number of surface structures or micro-surface structures, or some or all of the segments can include a different number of surface structures or micro-surface structures. The surface structures or micro-surface structures can be spaced equally or non-equally from one another on one or more of the segments. The segments are illustrated as being aligned parallel to the longitudinal axis of the inflatable device; however, it can be appreciated that one or more of the segments can be aligned perpendicular to the longitudinal axis of the inflatable device or in some other non-parallel orientation relative to the longitudinal axis of the inflatable device. FIGS. 10 and 11 illustrate longitudinal and radial bands 140, 150 of surface structures or micro-surface structures. The longitudinal bands are illustrated as being angularly spaced apart at equal angular amounts; however, it can be appreciated that one or more longitudinal bands can be spaced at non-equal angular amounts from one another. The longitudinal bands are illustrated as being all positioned parallel to the longitudinal axis of the inflatable balloon; however, it can be appreciated that one or more of the longitudinal bands can be positioned non-parallel to the longitudinal axis of the inflatable balloon. The number of surface structures or micro-surface structures on each longitudinal band can be the same, or one or more longitudinal bands can have a different number of surface structures or micro-surface structures. The surface structures or micro-surface structures can be spaced equally or non-equally from one another on one or more of the longitudinal bands. The longitudinal bands can have the same length, or one or more of the longitudinal bands can have a different length from one or more other longitudinal bands. The longitudinal bands illustrated in FIG. 10 are generally about the same length, each have generally the same number of surface structures or micro-surface structures, and extend about 70-100% of the longitudinal length of the inflatable balloon, typically about 80-100% of the longitudinal length of the inflatable balloon, and more typically about 90-100% of the longitudinal length of the inflatable balloon. As illustrated in FIG. 11, the radial bands 150 are illustrated as being spaced apart equal distances along the longitudinal length of the inflatable balloon; however, it can be appreciated that one or more radial bands can be spaced at non-equal distances from one another. The radial bands are illustrated as being all positioned generally perpendicular to the longitudinal axis of the inflatable balloon; however, it can be appreciated that one or more of the radial bands can be positioned non-perpendicular to the longitudinal axis of the inflatable balloon. The number of surface structures or micro-surface structures on each radial band can be the same, or one or more radial bands can have a different number of surface structures or micro-surface structures. The surface structures or micro-surface structures can be spaced equally or non-equally from one another on one or more of the radial bands. The radial bands can have the same length, or one or more of the radial bands can have a different length from one or more other radial bands. The radial bands illustrated in FIG. 11 extend about 70-100% about the circumference of the of the inflatable balloon, typically about 80-100% about the circumference of the inflatable balloon, and more typically about 90-100% about the circumference of the inflatable balloon. As described above, the inflatable balloon can include segments or surface structures or micro-surface structures. As can be appreciated, the outer surface of the inflatable balloon can include one or more segments, one or more longitudinal bands and/or one or more radial bands of surface structures or micro-surface structures. As defined herein, a segment has a length that is less than a longitudinal band or a radial band. A plurality of segments aligned together or closely together can form a longitudinal band or a radial band. The type and/or configuration of the surface structures or micro-surface structures on the one or more segments, longitudinal bands and/or radial bands is non-limiting. For example, the one or more segments, longitudinal bands can include one or more of the surface structures or micro-surface structures illustrated in FIGS. 2, 3, 5, 6, 7 and 9.

Figure 2:
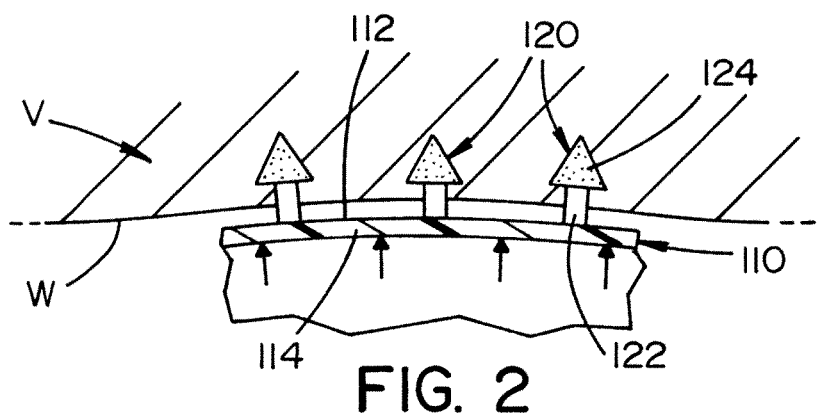
FIG. 2 is an enlarged sectional view of the inflation device of FIG. 1 showing a plurality of surface structures or micro-surface structures penetrating the inner wall of a body passageway during the inflation of the inflation device.
Figure 3:
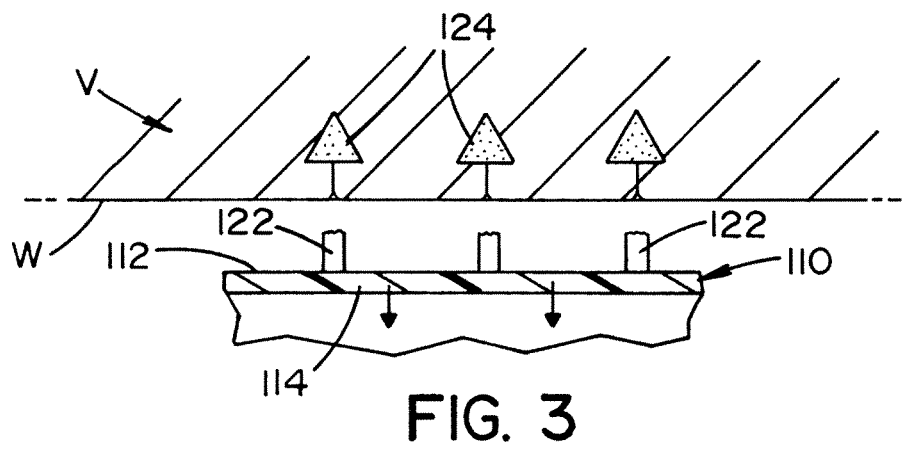
FIG. 3 is an enlarged sectional view of the inflation device of FIG. 2 showing a portion of a plurality of surface structures or micro-surface structures being retained in the inner wall of a body passageway during the deflation of the inflation device.
Figure 5:
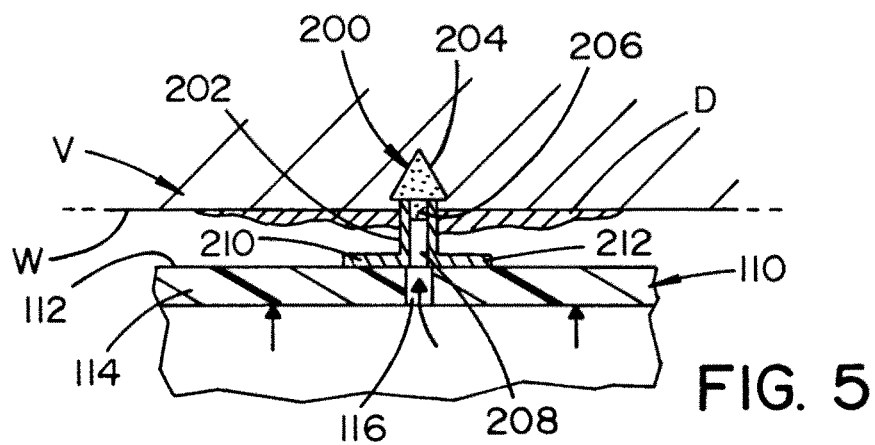
FIG. 5 is an enlarged sectional view of the inflation device showing another non-limiting embodiment of a plurality of surface structures or micro-surface structures penetrating the inner wall of a body passageway during the inflation of the inflation device.
Figure 6:
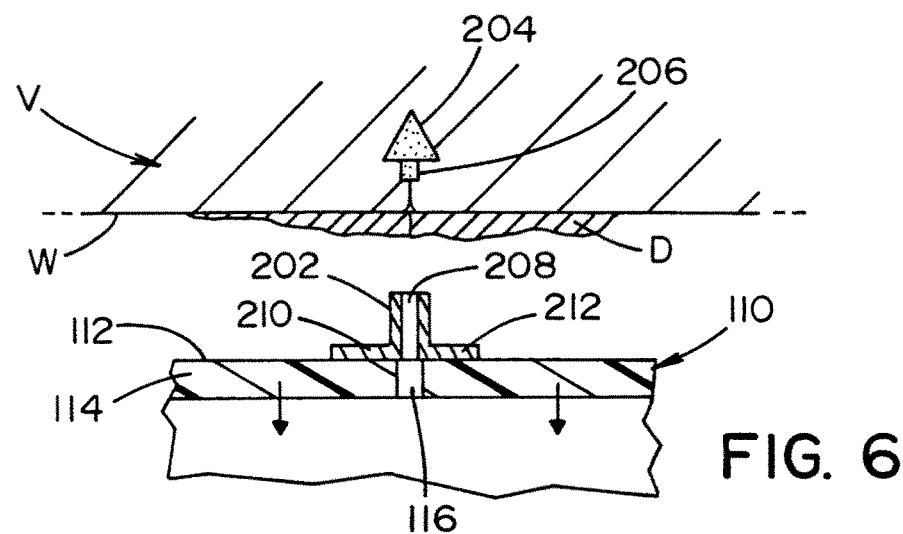
FIG. 6 is an enlarged sectional view of the inflation device of FIG. 5 showing a portion of a plurality of surface structures or micro-surface structures being retained in the inner wall of a body passageway during the deflation of the inflation device.

Referring now to FIGS. 1-3, there is illustrated one non-limiting configuration or surface structure or micro-surface structure that can be included on the outer surface of the inflatable balloon. The surface structure or micro-surface structure 120 includes a base portion 122 and a top portion 124. The based portion and the top portion can be formed of the same material or different material. As illustrated in FIGS. 2 and 3, the top portion is formed of a material that includes one or more biological agents. The top portion may also including one or more other materials such as a polymer; however, this is not required. The materials used to form the top portion are generally biodegradable and/or bioabsorbable materials. The shape of the top portion and base portion are non-limiting. As illustrated in FIGS. 1-3, the base portion has a generally uniform shape and thickness along a longitudinal length of the body portion; however, this is not required. The base portion is illustrated as being formed of a different material than the top portion; however, this is not required. The top portion is illustrated as having a sharp or pointed top; however, this is not required. Such a configuration is used to facilitate in penetrating a wall W of a body passageway V when the inflatable balloon is inflated. The top portion of the surface structures or micro-surface structures is illustrated as having a cone-shape or inverted top-shape which has an arrow-head cross-sectional profile as illustrated in FIG. 2. This type of configuration is used to facilitate in maintaining the top portion in the wall of the body passageway V when the inflatable balloon is deflated. As can be appreciated, many other configurations of the top portion can be used to facilitate in maintaining the top portion in the wall of the body passageway V when the inflatable balloon is deflated. In such configurations, a portion of the top portion is wider than the tip and/or extends outwardly from the side of the top portion so as to resist being drawn out from the wall of the body passageway after the wider portion and/or outward extension has penetrated the wall of the body passageway.

Referring now to FIGS. 2 and 3, the retention of the top portion of the surface structures or micro-surface structures in the body passageway V is illustrated. The arrows in FIG. 2 illustrate the movement of the wall 114 of the inflatable balloon toward the inner surface of wall W of the body passageway V (e.g., blood vessel, etc.) as the inflatable balloon is expanded. As illustrated in FIG. 2, the inflatable balloon has sufficiently expanded in the body passageway V to cause the top portion 124 and a portion of the base portion 122 of the surface structures or micro-surface structures 120 to penetrate through wall W of body passageway V. When the top portion 124 includes one or more biological agents, the penetration of the top portion into the body passageway results in localized delivery of one or more biological agents into a treatment area of the body passageway. The composition of the top portion can be such as to provide an immediate and/or controlled release of one or more biological agents in the body passageway. The base portion can also include one or more biological agents; however, this is not required. The composition of the base portion and the top portion can be the same or different. As illustrated in FIGS. 2 and 3, the composition of the top portion is different from the composition of the base portion. FIG. 2 illustrates that the base portion of the surface structures or micro-surface structures is generally the same length; however, it can be appreciated that the base portion of one or more surface structures or micro-surface structures can be different such that the top portion of one or more surface structures or micro-surface structures penetrates a differing depth into the body passageway as compared to one or more other surface structures or micro-surface structures. As can also be appreciated, the base portion can optionally be eliminated or the length of the base portion can be such that the top portion does not fully penetrate though the inner surface of the wall of the body portion; however, this is not required.

Referring now to FIG. 3, the inflatable balloon is being deflated as indicated by the arrows. As the inflatable balloon is deflated, the wall 114 of the inflatable balloon moves away from or retracts from the inner surface of wall W. Due to the configuration of the top portion 124 of the surface structures or micro-surface structures that have penetrated into the body passageway, the top portions resist being pulled out of the body passageway thereby resulting in the top portions partially or fully breaking off from or released from the base portion and remaining partially or fully embedded in the wall of the body passageway. As can be appreciated, the base portion can be also or alternatively be designed to break-off of or release from the outer surface of the inflatable balloon; however, this is not required. The top portion and/or the base portion can include one or more structures (e.g., notch, narrowed portion, slot, etc.) that facilitates in the partially or fully breaking off or release of the top portion from the base portion; however, this is not required. Additionally or alternatively, the base portion and/or a portion of the top portion can be formed of one or more materials that facilitates in the partially or fully breaking off or release of the top portion from the base portion; however, this is not required. Furthermore, the base portion and/or a portion of the top portion can additionally or alternatively be formed in a manner (e.g., base portion a hollow tube, etc.) that facilitates in the partially or fully breaking off or release of the top portion from the base portion; however, this is not required. The material that is used to form the top portion is generally different from the material that forms the wall 114 of the inflatable device; however, this is not required. Likewise, the material that is used to form the base portion is generally different from the material that forms the wall 114 of the inflatable device; however, this is not required. A portion or all of the one or more surface structures or micro-surface structures are generally gown on the outer surface of the inflatable balloon, molded on the outer surface of the inflatable balloon, and/or bonded to the outer surface of the inflatable balloon.

Referring now to FIGS. 5 and 6, there is illustrated another non-limiting configuration of surface structure or micro-surface structure that can be included on the outer surface of the inflatable balloon. The surface structure or micro-surface structure 200 includes a base portion 202 and a top portion 204. The based portion and the top portion can be formed of the same material or different material. As illustrated in FIGS. 5 and 6, the top portion is formed of a material that includes one or more biological agents. The top portion may also including one or more other materials such as a polymer; however, this is not required. The materials used to form the top portion are generally biodegradable and/or bioabsorbable materials. The shape of the top portion and base portion are non-limiting. As illustrated in FIGS. 5 and 6, the base portion has a generally uniform shape and thickness along a longitudinal length of the body portion; however, this is not required. The base portion is illustrated as being formed of a different material than the top portion; however, this is not required. The top portion is illustrated as having a sharp or pointed top; however, this is not required. Such a configuration is used to facilitate in penetrating wall W of a body passageway V when the inflatable balloon is inflated. The top portion of the surface structures or micro-surface structures is illustrated as having a cone-shape or inverted top-shape which has an arrow-head cross-sectional profile as illustrated in FIGS. 5 and 6. This type of configuration is used to facilitate in maintaining the top portion in the wall of the body passageway V when the inflatable balloon is deflated. As can be appreciated, many other configurations of the top portion can be used to facilitate in maintaining the top portion in the wall of the body passageway V when the inflatable balloon is deflated. In such configurations, a portion of the top portion is wider than the tip and/or extends outwardly from the side of the top portion so as to resist being drawn out from the wall of the body passageway after the wider portion and/or outward extension has penetrated the wall of the body passageway. The top portion is illustrated as including a bottom leg 206 that is designed to be inserted into a passageway 208 in the base portion. The size and shape of leg 206 is generally selected so that the top portion remains connected to the base portion while the inflatable balloon is transported to a treatment area in the body passageway. The leg is illustrated as being formed of the same material as the remaining portion of the top portion; however, this is not required. The leg is illustrated as having a thinner width than the base region of the cone-shape or inverted top-shape portion of the top portion. Such a configuration allows the base region to rest on the upper edge of the base portion while the leg 206 is positioned in passageway 208 in the base portion. The base portion is illustrated as having two legs 210, 212; however, this is not required. The two legs can be used to provide support to the base portion and/or facilitate in securing the base portion to the outer surface of the inflatable device. The passageway 208 in the base portion is illustrated as being positioned at least partially over an opening 116 in the wall 114 of the inflatable balloon. As can be appreciated, the passageway 208 in the base portion of one or more surface structures or micro-surface structures may not be positioned at least partially over an opening in the wall of the inflatable balloon.

FIG. 5 illustrates the insertion of the top portion into the wall of the body passageway. The arrows in FIG. 5 illustrate the movement of wall 114 of the inflatable balloon toward the inner surface of wall W of the body passageway V (e.g., blood vessel, etc.) as the inflatable balloon is expanded. As illustrated in FIG. 5, the inflatable balloon has sufficiently expanded in the body passageway V to cause the top portion 204 and a portion of the base portion 202 of the surface structures or micro-surface structures 200 to penetrate through the diseased region D and into wall W of body passageway V. When the top portion 204 includes one or more biological agents, the penetration of the top portion into the body passageway results in localized delivery of one or more biological agents into a treatment area of the body passageway. The composition of the top portion can be such as to provide an immediate and/or controlled release of one or more biological agents in the body passageway. The base portion can also include one or more biological agents; however, this is not required. The composition of the base portion and the top portion can be the same or different. As illustrated in FIGS. 5 and 6, the composition of the top portion is different from the composition of the base portion. FIG. 5 illustrates that the base portion of the surface structures or micro-surface structures is generally the same length; however, it can be appreciated that the base portion of one or more surface structures or micro-surface structures can be different such that the top portion of one or more surface structures or micro-surface structures penetrates a differing depth into the body passageway as compared to one or more other surface structures or micro-surface structures. As can also be appreciated, the base portion can optionally be eliminated or the length of the base portion can be such that the top portion does not fully penetrate though the inner surface of the wall of the body portion; however, this is not required.

As illustrated by the arrows in FIG. 5, as the inflatable balloon is inflated by fluid, the pressure inside the inflatable balloon will increase. Some of this pressure increase will translate through opening 116 and create a force on the bottom of leg 206 of the top portion. The top portion can be designed to partially or fully disengage from the base portion when sufficient force is applied on the bottom of leg 206. The size and shape of leg 206 and passageway 208 can be selected so that a predetermined pressure inside the inflatable balloon will result in the partially or fully disengagement of leg 206 from the base portion; however, this is not required. The pressure applied to leg 208 can also be used to cause the top portion to further penetrate into the wall of the body passageway and/or inhibit or present the top portion from partial or fully withdrawal from the body passageway when the inflatable balloon is deflated and withdrawn from the body passageway; however, this is not required. In addition to the localized application of biological agent in the body passageway by the top portion, a burst of biological agent can also be injected onto and/or into the body passageway via opening 116 and passageway 208. For example, the fluid being flowed into the inflatable balloon to inflate and/or maintain the inflation of the inflatable balloon can include one or more biological agents; however, this is not required. As such, the one or more biological agents can pass through opening 116 and through passageway 208 to apply such biological agent to the inner wall surface of the body passageway and/or into the wall of the body passageway.

Referring now to FIG. 6, the inflatable balloon is being deflated as indicated by the arrows. As the inflatable balloon is deflated, the wall 114 of the inflatable balloon moves away from or retracts from the inner surface of wall W. Due to the configuration of the top portion 204 of the surface structures or micro-surface structures that have penetrated into the body passageway, the top portions resist being pulled out of the body passageway thereby remaining partially or fully embedded in the wall of the body passageway. The material that is used to form the top portion is generally different from the material that forms the wall 114 of the inflatable device; however, this is not required. Likewise, the material that is used to form the base portion is generally different from the material that forms the wall 114 of the inflatable device; however, this is not required. A portion or all of the one or more surface structures or micro-surface structures are generally grown on the outer surface of the inflatable balloon, molded on the outer surface of the inflatable balloon, and/or bonded to the outer surface of the inflatable balloon.

Figure 7:
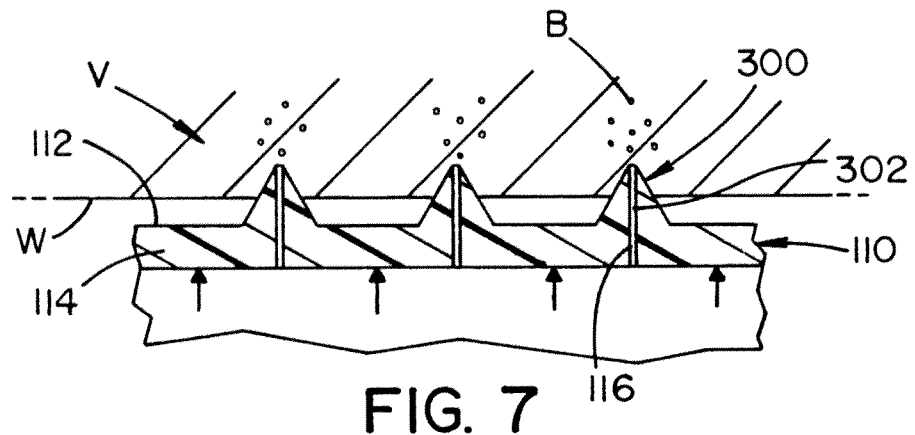
FIG. 7 is an enlarged sectional view of the inflation device showing another non-limiting embodiment of a plurality of surface structures or micro-surface structures penetrating the inner wall of a body passageway during the inflation of the inflation device.
Figure 8:
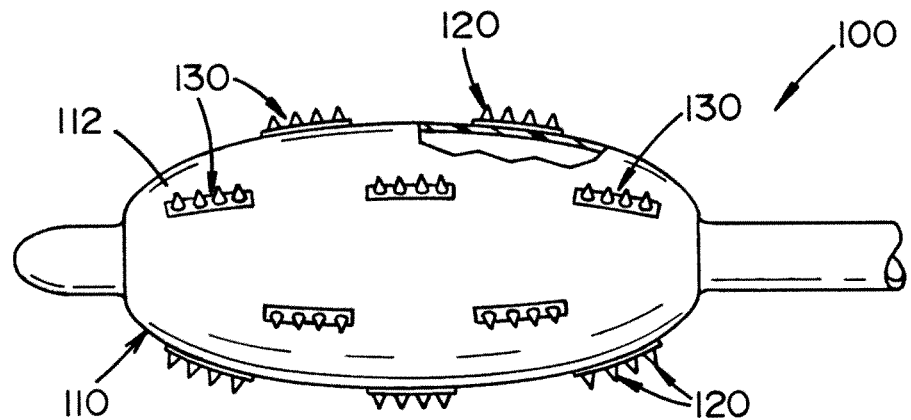
FIG. 8 is a side view of an inflatable device that includes another non-limiting embodiment of a plurality of surface structures or micro-surface structures organized in a certain pattern on the outer surface of the inflatable device in accordance with the present invention.

Referring now to FIG. 7, there is illustrated another non-limiting configuration of surface structure or micro-surface structure that can be included on the outer surface of the inflatable balloon. The surface structure or micro-surface structure 300 can be formed of one or more biological agents and/or one or more other materials such as a polymer; however, this is not required. The materials used to form the surface structure or micro-surface structure are generally biodegradable and/or bioabsorbable materials. The shape of the surface structure or micro-surface structure is non-limiting. As illustrated in FIG. 7, the surface structure or micro-surface structure has a generally pyramidal shape; however, this is not required. The surface structure or micro-surface structure is illustrated as being formed of similar material as the wall 114 of the inflatable balloon; however, this is not required. The top region of the surface structure or micro-surface structure portion is illustrated as having a sharp or pointed top; however, this is not required. Such a configuration is used to facilitate in penetrating wall W of a body passageway V when the inflatable balloon is inflated. The surface structure or micro-surface structure is illustrated as including a passageway 302 that is positioned at least partially over an opening 116 in the wall 114 of the inflatable balloon. As can be appreciated, the passageway 302 in one or more surface structures or micro-surface structures may not be positioned at least partially over an opening in the wall of the inflatable balloon. As can be appreciated, one or more of the surface structure or micro-surface structure can be absent passageway 302. The height of the surface structure or micro-surface structure is illustrated as being the same; however, this is not required.

FIG. 7 illustrates the insertion of the top region of the surface structure or micro-surface structure into the wall of the body passageway. The arrows in FIG. 7 illustrate the movement of wall 114 of the inflatable balloon toward the inner surface of wall W of the body passageway V (e.g., blood vessel, etc.) as the inflatable balloon is expanded. As illustrated in FIG. 7, the inflatable balloon has sufficiently expanded in the body passageway V to cause the top region of the surface structures or micro-surface structures 300 to penetrate through and into wall W of body passageway V. When the top region of the surface structure or micro-surface structure includes one or more biological agents, the penetration of the top region into the body passageway results in localized delivery of one or more biological agents into a treatment area of the body passageway. The composition of the top region of the surface structure or micro-surface structure can be such so as to provide an immediate and/or controlled release of one or more biological agents in the body passageway.

As the inflatable balloon is inflated by fluid, a portion of the fluid can flow through opening 116 and through passageway 302 to provide a burst of biological agent to the treatment area of the body passageway and/or inject biological agent onto and/or into the body passageway via opening 116 and passageway 302; however, this is not required. For example, the fluid being flowed into the inflatable balloon to inflate and/or maintain the inflation of the inflatable balloon can include one or more biological agents; however, this is not required. As such, the one or more biological agents can pass through opening 116 and though passageway 302 to apply such biological agent to the inner wall surface of the body passageway and/or into the wall of the body passageway.

A portion or all of the one or more surface structures or micro-surface structures are generally grown on the outer surface of the inflatable balloon, molded on the outer surface of the inflatable balloon, formed with the inflatable balloon, and/or bonded to the outer surface of the inflatable balloon. The surface structures or micro-surface structures illustrated in FIG. 7 are not designed to break off from the outer surface of the inflatable balloon and be partially retained in the wall of the body passageway; however, it can be appreciated that all or a portion of the surface structures or micro-surface structures can break off or be released form the outer surface of the inflatable balloon and be partially retained in the wall of the body passageway.

Figure 9:
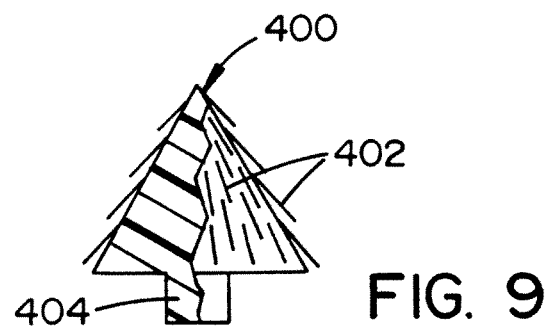
FIG. 9 is an enlarged view of the top portion of another non-limiting embodiment of a surface structure or micro-surface structures in accordance with the present invention.

Referring now to FIG. 9 there is illustrated a top portion 400 of a surface structure or micro-surface structure that includes one or more fibers, barbs, etc. 402 and a leg 404. As can be appreciated, the leg is an optional feature, and/or the leg can represent a portion of a base portion of the surface structure or micro-surface structure. The general configuration of the top portion 400 is similar to the configuration of top portion 204 illustrated in FIGS. 5 and 6 and top portion 124 in FIGS. 1-3, thus will not be further described herein. The top portion 400 can include one or more biological agents; however, this is not required. The one or more fibers, barbs, etc. 402 are used to facilitate in maintaining the top portion partially or fully in the wall of the body passageway once the top portion has partially or fully penetrated into the wall of the body passageway. The one or more fibers, barbs, etc. can be formed of biological agent; however, this is not required. The materials used to form the top portion are generally bioabsorbable and/or biodegradable. The one or more fibers, barbs, etc. 402 are illustrated as angling downwardly so as to not impair the insertion of the top portion into the wall of the body passageway, but angled to impair or prevent withdrawal of the top portion from the wall of the body passageway.

Figure 4:
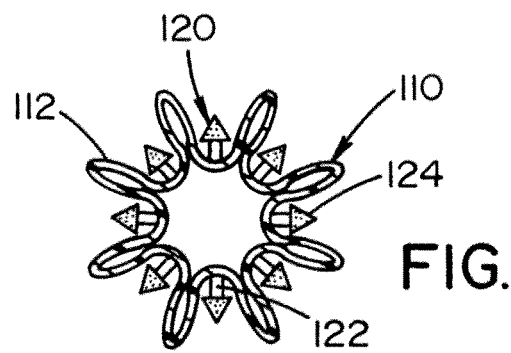
FIG. 4 is a cross-sectional view of an inflation device of the present invention in a deflated state and wherein the inflatable device includes a plurality of surface structures or micro-surface structures on the outer surface of the inflatable device that are protected within the folds of the deflated inflation device.

Referring now to FIG. 4, some or all of the surface structures or micro-surface structures can be protected from damage by designing and positioning one or more surface structures or micro-surface structures to be positioned between the folds of the inflatable device when the inflatable device is in a fully or partially uninflated state. As illustrated in FIG. 4, the top edge of the top portion of the surface structures or micro-surface structures is positioned beneath the folds of the inflatable device so that when the inflatable balloon is positioned in the body passageway, the protected surface structures or micro-surface structures are protected or shielded from engaging with the inner surface of the wall of the body passageway, thereby reducing the incidence of damage to the surface structures or micro-surface structures prior to the positioning of the inflatable balloon at the treatment area. As can be appreciated, one or more of the surface structures or micro-surface structures can also or alternatively be partially or fully protected by a protective coating; however, this is not required. As illustrated in FIG. 4, the surface structures or micro-surface structures are positioned in the valleys of the folds of the inflatable balloon; however, it can be appreciated that one or more of the surface structures or micro-surface structures can be positioned on the sides of the folds of the inflatable balloon and still be at least partially protected by such folds. The surface structures or micro-surface structures illustrated in FIG. 4 is the same or similar to the surface structures or micro-surface structures illustrated in FIGS. 1-3; however, it will be appreciated that other or additional types of surface structures or micro-surface structures can be positioned in the folds of the inflatable balloon. Examples of some of the other configurations of surface structures or micro-surface structures that can be used are illustrated in FIGS. 5-7 and 9.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

What is claimed is:

1. A medical device for insertion and inflation in a body passageway, said medical device including an inflatable device that is designed to be inflated and deflated while positioned in the body passageway, said inflatable device is inflatable by inserting a fluid in an internal cavity of an inflatable body of said inflatable device, said inflatable body having an outer surface, said outer surface includes a surface structure or micro-surface structure that is configured to at least partially penetrate into an inner wall of the body passageway when said inflatable device is inflated, said surface structure or micro-surface structure includes a top portion, said top portion formed of a biodegradeble or bioabsorbable material, said top portion including a biological agent, said top portion including an upper region and a narrow region, said narrow region having a cross-section size that is less than a cross-section size of said upper region where said narrow region connects to said upper region, said top portion is configured to detach from a lower body of said surface structure or micro-surface structure at a narrow region of said top portion, said lower body including a base that engages said inflatable body and an upper region having a cavity, said cavity configured to telescopically receive at least a portion of said narrow region of said top portion.

2. The medical device as defined in claim 1, wherein said lower body of said surface structure or micro-surface structure includes an internal passageway, said internal passageway fluidly connected to said internal cavity of said inflatable body to enable fluid to flow from said internal cavity and through said internal passageway of said body portion of said surface structure, said fluid flow through said internal passageway at least partially causing said top portion of said surface structure or micro-surface structure to release from said lower body of said surface structure or micro-surface structure.

3. The medical device as defined in claim 1, wherein said top portion is configured to resist detachment from the body passageway once said top portion has penetrated into the wall of the body passageway, said top portion a) having a top-shaped portion, b) having an arrow-head shaped portion, c) including a barb, d) including non-smooth surfaces, e) including angled fibers, f) including a spike, or some combination of a)-f) that facilitate in resisting detachment of said top portion from the body passageway.

4. The medical device as defined in claim 1, wherein said outer surface of said inflatable body of said inflatable device includes a plurality of said surface structures or micro-surface structures, said plurality of said surface structures or micro-surface structures a) positioned and spaced uniformly on said outer surface of said inflatable body of said inflatable device, b) positioned and spaced non-uniformly on said outer surface of said inflatable body of said inflatable device, c) positioned only on certain regions on said outer surface of said inflatable body of said inflatable device, d) positioned in bands on said outer surface of said inflatable body of said inflatable device, or some combination of a)-d).

5. A method of delivering a biological agent to a body passageway including:

providing inflatable device having an inflatable body, said inflatable body including at least one surface structure or micro-surface structure located on an outer surface of said inflatable body, said at least one surface structure or micro-surface structure configured to at least partially penetrate into an inner wall of the body passageway when said inflatable device is inflated, said surface structure or micro-surface structure includes a top portion, said top portion formed of a biodegradable or bioabsorbable material, said top portion including biological agent, said top portion including an upper region and a narrow region, said narrow region having a cross-section size that is less than a cross-section size of said upper region where said narrow region connects to said upper region, said top portion is configured to detach from a lower body of said surface structure or micro-surface structure at a narrow region of said top portion, said lower body including a base that engages said inflatable body and an upper region having a cavity, said cavity configured to telescopically receive at least a portion of said narrow region of said top portion;

positioning said inflatable device in the body passageway while said inflatable device is not fully inflated;

inserting fluid into an inner cavity of said inflatable body of said inflatable device to cause said inflatable body to inflate and to expand such that at least a part of said top portion of at least one of said surface structures or micro-surface structures penetrates an inner surface wall of said body passageway;

locally delivering biological agent to said inner surface wall of said body passageway by said at least one surface structure or micro-surface structure via said penetration of said top portion of said surface structure or micro-surface structure into said body passageway;

at least partially deflating said inflatable body to cause said top portion of said at least one surface structure or micro-surface structure that has penetrated into said body passageway to slidably separate from said upper region of said lower body of said at least one surface structure or micro-surface structure; and, removing said inflatable device from said body passageway while at least a portion of said at least one surface structure or micro-surface structure remains in said body passageway.

6. The method as defined in claim 5, wherein said body portion of said surface structure or micro-surface structure includes an internal passageway, said internal passageway fluidly connected to said internal cavity of said inflatable body to enable fluid to flow from said internal cavity and through said cavity of said lower body of said surface structure, said fluid flow through said cavity of said lower body at least partially causing said top portion of said surface structure or micro-surface structure to release from said lower body of said surface structure or micro-surface structure.

7. The method as defined in claim 6, wherein said top portion is configured to detach from or break-off from a body portion of said surface structure or micro-surface structure after being a) subjected to a certain amount of fluid pressure from fluid in said internal cavity, b) subjected to electrical current, c) subjected to electromagnetic radiation, d) subjected to a chemical reaction, e) subjected to ultrasonic waves, or some combination of a)-e).

* * * * *